(12) United States Patent
Palushi et al.

(10) Patent No.: US 12,121,686 B2
(45) Date of Patent: Oct. 22, 2024

(54) DILATION CATHETER WITH REMOVABLE BULB TIP

(71) Applicant: Acclarent, Inc., Irvine, CA (US)

(72) Inventors: Jetmir Palushi, Irvine, CA (US); Azhang Hamlekhan, Irvine, CA (US); John H. Thinnes, Jr., Mission Viejo, CA (US)

(73) Assignee: Acclarent, Inc., Irvine, CA (US)

( * ) Notice: Subject to any disclaimer, the term of this patent is extended or adjusted under 35 U.S.C. 154(b) by 463 days.

(21) Appl. No.: 17/580,729

(22) Filed: Jan. 21, 2022

(65) Prior Publication Data

US 2022/0211986 A1 Jul. 7, 2022

Related U.S. Application Data

(62) Division of application No. 16/003,178, filed on Jun. 8, 2018, now Pat. No. 11,260,208.

(51) Int. Cl.
*A61M 29/02* (2006.01)
*A61B 17/24* (2006.01)
(Continued)

(52) U.S. Cl.
CPC ............ *A61M 29/02* (2013.01); *A61B 17/24* (2013.01); *A61B 17/3415* (2013.01);
(Continued)

(58) Field of Classification Search
None
See application file for complete search history.

(56) References Cited

U.S. PATENT DOCUMENTS 4,015,607 A * 4/1977 Wright, III .......... A61M 27/002
623/23.64
9,155,492 B2 10/2015 Jenkins et al.
(Continued)

FOREIGN PATENT DOCUMENTS

| CN | 101917916 A | 12/2010 |
|---|---|---|
| CN | 107185097 A | 9/2017 |
| WO | WO 2016/160815 A1 | 10/2016 |

OTHER PUBLICATIONS

Second Chinese Office Action dated Oct. 27, 2022, for Application No. 201980038301.4, 6 pages.
(Continued)

*Primary Examiner* — Shaun L David
(74) *Attorney, Agent, or Firm* — Morgan, Lewis & Bockius LLP

(57) ABSTRACT

An apparatus includes a shaft, an expandable dilation member, and a bulbous tip. The shaft has a first outer cross-sectional dimension. The dilation member is positioned proximal to the distal end of the shaft. The dilation member is operable to transition between a non-expanded configuration and an expanded configuration. The dilation member is sized to pass through a passageway associated with drainage of a paranasal sinus or a Eustachian tube when the dilation member is in the non-expanded configuration. The bulbous tip is positioned at the distal end of the shaft. The bulbous tip is distal to the dilation member. The bulbous tip has a second outer cross-sectional dimension. The second outer cross-sectional dimension is larger than the first outer cross-sectional dimension. The bulbous tip is removably secured to the distal end of the shaft.

20 Claims, 8 Drawing Sheets

(51) Int. Cl.
*A61B 17/34* (2006.01)
*A61B 90/00* (2016.01)
*A61M 25/10* (2013.01)

(52) U.S. Cl.
CPC .... *A61M 25/1002* (2013.01); *A61M 25/1025* (2013.01); *A61B 2090/062* (2016.02); *A61M 2025/1054* (2013.01); *A61M 2025/1061* (2013.01); *A61M 2029/025* (2013.01); *A61M 2210/0675* (2013.01); *A61M 2210/0681* (2013.01)

(56) References Cited

U.S. PATENT DOCUMENTS

| | | | |
|---|---|---|---|
| 10,610,308 B2 | 4/2020 | Sema et al. | |
| 11,260,208 B2 | 3/2022 | Palushi et al. | |
| 2008/0172033 A1 | 7/2008 | Keith et al. | |
| 2008/0183128 A1 | 7/2008 | Morriss et al. | |
| 2010/0274188 A1* | 10/2010 | Chang | A61B 8/12 606/167 |
| 2011/0004057 A1 | 1/2011 | Goldfarb et al. | |
| 2012/0095397 A1 | 4/2012 | Konstantino et al. | |
| 2013/0274715 A1* | 10/2013 | Chan | A61B 17/22 604/514 |
| 2013/0317305 A1 | 11/2013 | Stevenson et al. | |
| 2014/0074141 A1 | 3/2014 | Johnson et al. | |
| 2014/0364725 A1 | 12/2014 | Makower | |
| 2015/0202089 A1* | 7/2015 | Campbell | A61B 5/411 600/478 |
| 2015/0374963 A1* | 12/2015 | Chan | A61F 11/20 606/192 |
| 2016/0008083 A1 | 1/2016 | Kesten et al. | |
| 2016/0015944 A1* | 1/2016 | Jenkins | A61M 25/09041 604/528 |
| 2016/0271375 A1 | 9/2016 | Chandler et al. | |
| 2016/0287059 A1* | 10/2016 | Ha | A61M 29/02 |
| 2016/0287445 A1* | 10/2016 | Wasicek | A61M 29/02 |
| 2017/0056632 A1 | 3/2017 | Jenkins et al. | |
| 2017/0120020 A1 | 5/2017 | Lin et al. | |
| 2017/0259043 A1* | 9/2017 | Chan | A61M 29/02 |
| 2019/0126007 A1 | 5/2019 | Vogelbaum | |
| 2019/0192176 A1 | 6/2019 | Palushi et al. | |
| 2019/0192177 A1 | 6/2019 | Palushi et al. | |

OTHER PUBLICATIONS

Chinese Office Action and Search Report dated May 13, 2022, for Application No. 201980038301.4, 8 pages.
International Search Report and Written Opinion dated Oct. 14, 2019, for International Application No. PCT/IB2019/054237, 19 pages.
U.S. Appl. No. 62/555,841, entitled "Adjustable Instrument for Dilation of Anatomical Passageway," filed Sep. 8, 2017.

* cited by examiner

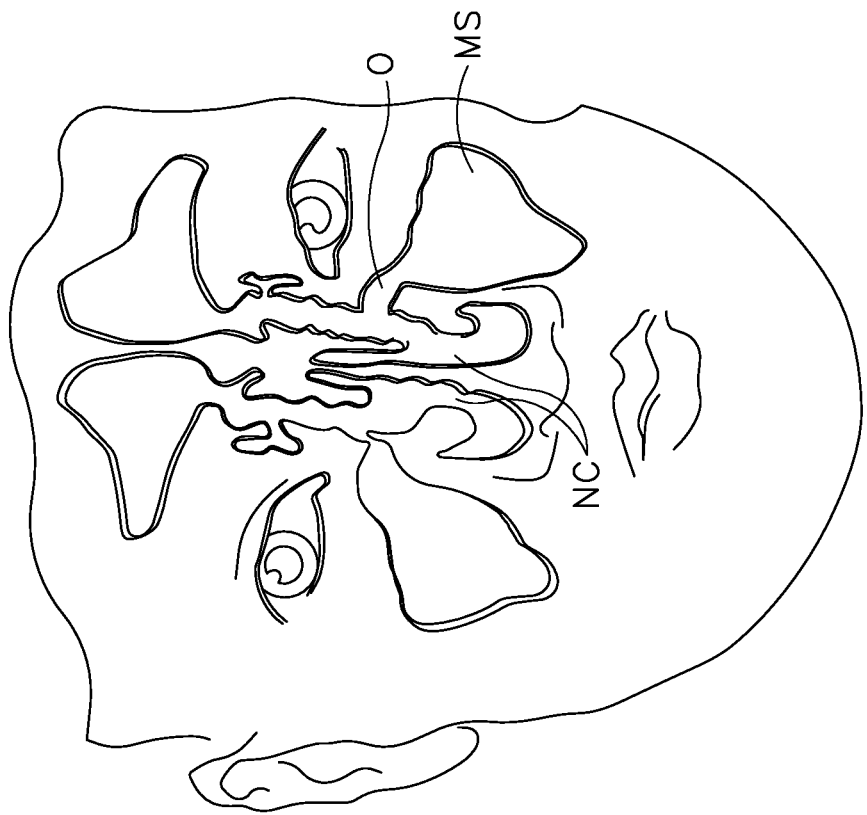
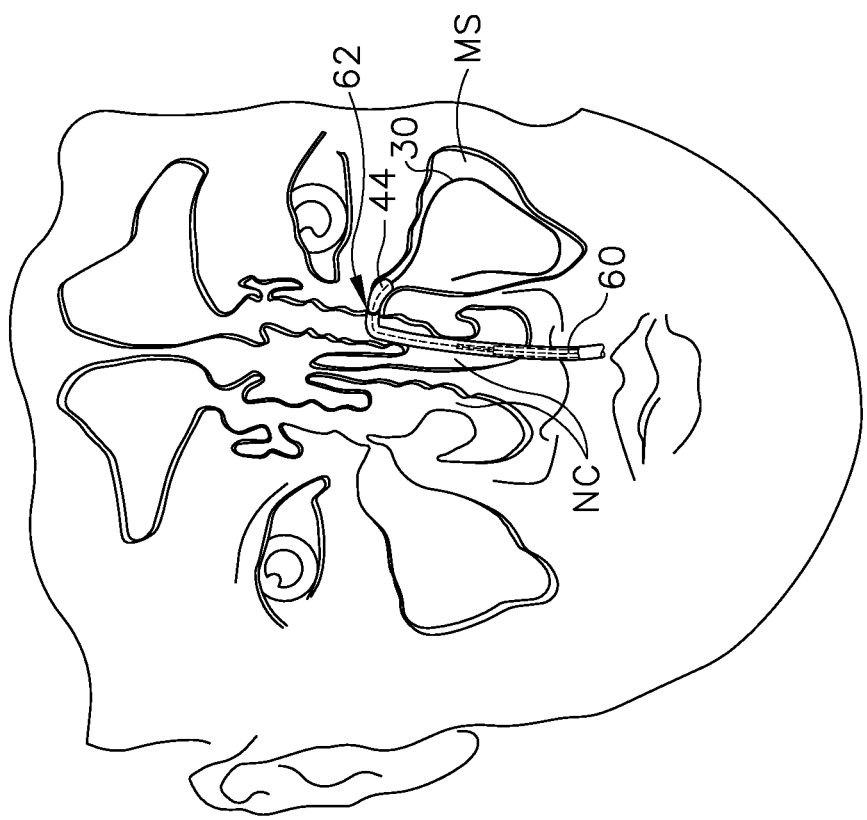

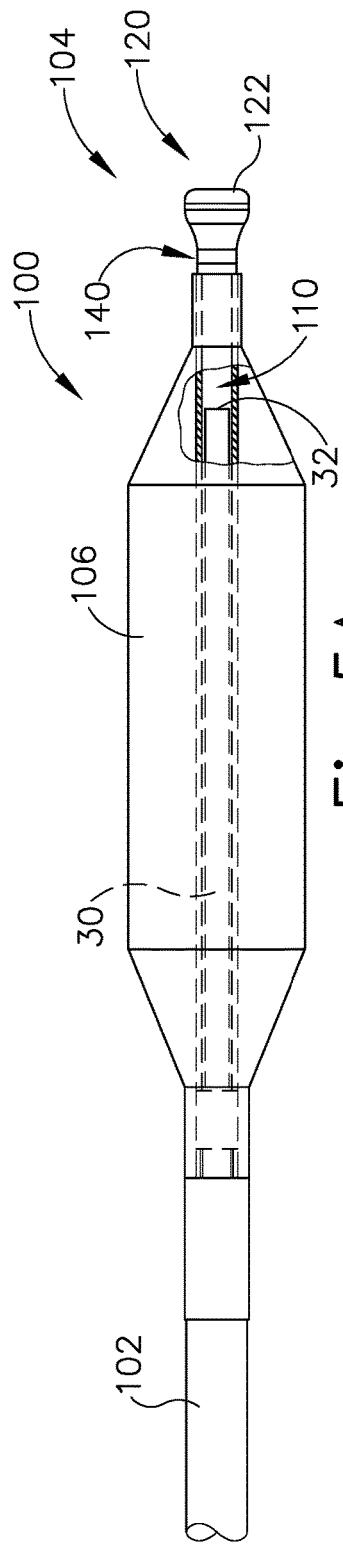
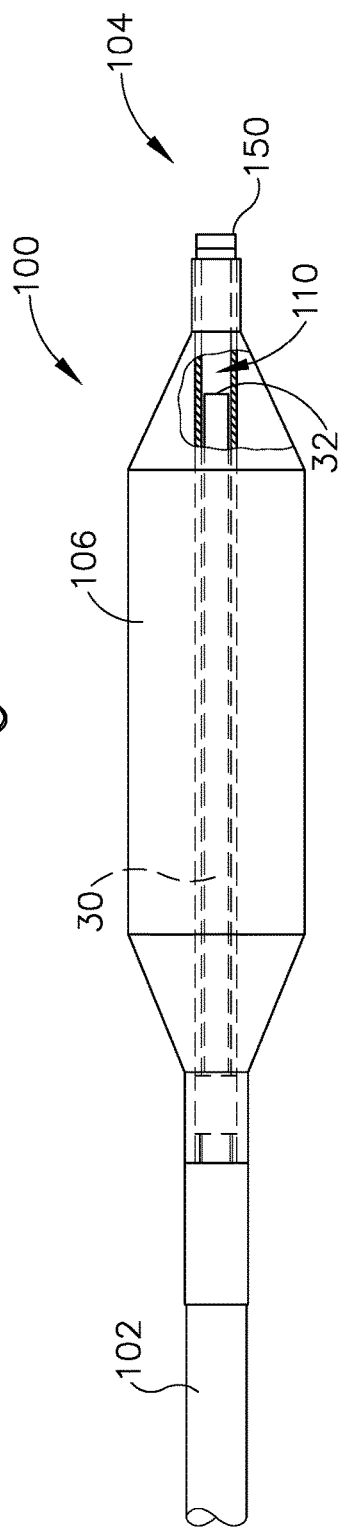
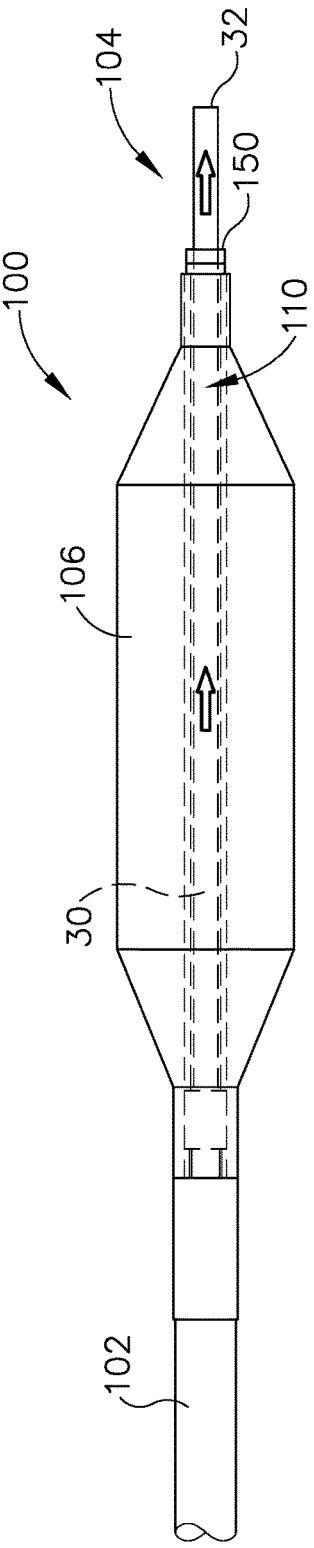
Fig.5A
Fig.5B
Fig.5C

DILATION CATHETER WITH REMOVABLE BULB TIP

This application is a continuation of U.S. application Ser. No. 16/003,178, filed Jun. 8, 2018, entitled "Dilation Catheter with Removable Bulb Tip," issued as U.S. Pat. No. 11,260,208 on Mar. 1, 2022.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, California.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle ear and further provide improved drainage from the middle ear to the nasopharynx. Methods and devices for dilating the Eustachian tube are disclosed in U.S. Patent Pub. No. 2010/0274188, entitled "Method and System for Treating Target Tissue within the ET," published on Oct. 28, 2010, now abandoned, the disclosure of which is incorporated by reference herein; and U.S. Patent Pub. No. 2013/0274715, entitled "Method and System for Eustachian Tube Dilation," published on Oct. 17, 2013, now abandoned, the disclosure of which is incorporated by reference herein. An example of such a system is the Aera® Eustachian Tube Balloon Dilation System by Acclarent, Inc. of Irvine, California.

Some dilation catheters may be particularly configured to transition between two modes particularly suited for two different kinds of medical procedures-one mode particularly suited for Eustachian tube dilation procedures and another mode particularly suited for sinus ostium dilation procedures. An example of such a dilation catheter is described in U.S. Pub. No. 2017/0056632, entitled "Dilation Catheter with Expandable Stop Element," published Mar. 2, 2017, issued as U.S. Pat. No. 10,512,763 on Dec. 24, 2019, the disclosure of which is incorporated by reference herein.

While several systems and methods have been made and used in ENT procedures, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 2A depicts a schematic view of a guide catheter, guidewire, and dilation catheter of the dilation instrument system of FIG. 1A inserted through the nose of a patient, with the guidewire positioned in a paranasal sinus cavity, and the dilator being expanded to dilate an ostium of the paranasal sinus cavity;

FIG. 2B depicts a schematic view of the patient of FIG. 2A, with the ostium of the paranasal sinus cavity in a dilated state;

FIG. 5A depicts a side elevational view of the distal portion of the dilation catheter of FIG. 4, with the bulb tip secured at the distal end of the dilation catheter, and with a guidewire at a proximal position within the dilation catheter;

FIG. 5B depicts a side elevational view of the distal portion of the dilation catheter of FIG. 4, with the bulb tip removed from the distal end of the dilation catheter, and with the guidewire at a proximal position within the dilation catheter;

FIG. 5C depicts a side elevational view of the distal portion of the dilation catheter of FIG. 4, with the bulb tip removed from the distal end of the dilation catheter, and with the guidewire at a distal position such that a distal end of the guidewire is distal to the distal end of the dilation catheter;

Figure 1A:
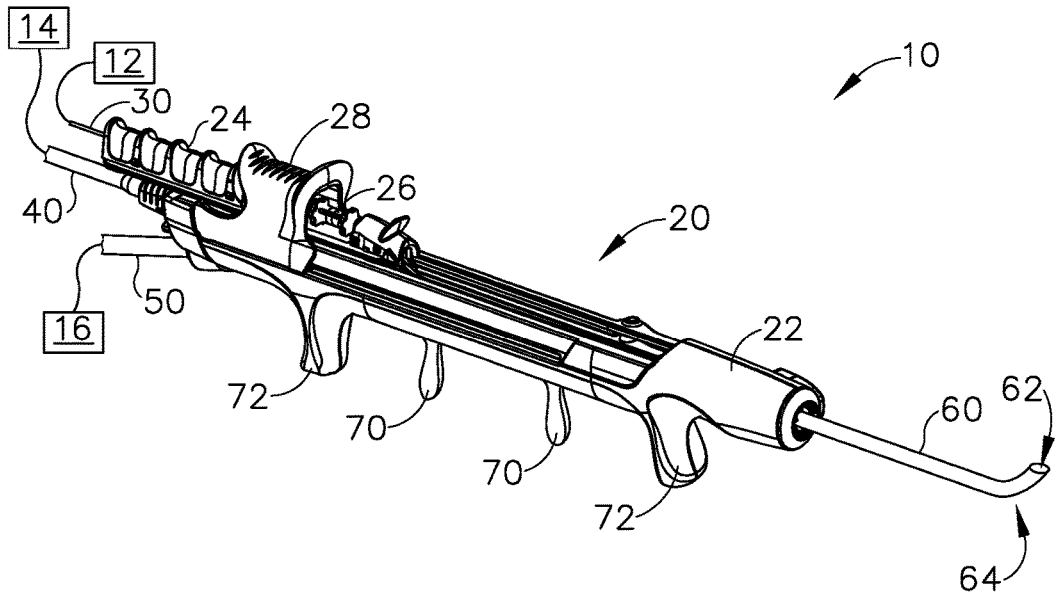
FIG. 1A depicts a perspective view of an exemplary dilation instrument system including a dilation instrument having a guidewire and a dilation catheter, showing the guidewire in a proximal position, and the dilation catheter in a proximal position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. EXEMPLARY DILATION INSTRUMENT SYSTEM

FIGS. 1A-1D show an exemplary dilation instrument system (10) that may be used to dilate the ostium of a paranasal sinus in a human patient, to dilate some other passageway associated with drainage of a paranasal sinus in a human patient; to dilate a Eustachian tube in a human patient; or to dilate some other anatomical passageway (e.g., within the ear, nose, or throat, etc.) in a human patient. Dilation instrument system (10) of this example comprises a guidewire power source (12), an inflation fluid source (14), an irrigation fluid source (16), and a dilation instrument (20). In some versions, guidewire power source (12) comprises a source of light. In some other versions, guidewire power source (12) is part of an image guided surgery (IGS) system. Inflation fluid source (14) may comprise a source of saline or any other suitable source of fluid. Irrigation fluid source (16) may also comprise a source of saline or any other suitable source of fluid.

Dilation instrument (20) of the present example comprise a handle body (22) with a guidewire slider (24), a guidewire spinner (26), and a dilation catheter slider (28). Handle body (22) is sized and configured to be gripped by a single hand of a human operator. Sliders (24, 28) and spinner (26) are also positioned and configured to be manipulated by the same hand that grasps handle body (22).

A guide catheter (60) extends distally from handle body (22). Guide catheter (60) includes an open distal end (62) and a bend (64) formed proximal to open distal end (62). In some versions, dilation instrument (20) is configured to removably receive several different kinds of guide catheters (60), each guide catheter (60) having a different angle formed by bend (64). Guide catheter (60) of the present example is formed of a rigid material (e.g., rigid metal and/or rigid plastic, etc.), such that guide catheter (60) maintains a consistent configuration of bend (64) during use of dilation instrument (20). In some versions, dilation instrument (20), is further configured to enable rotation of guide catheter (60), relative to handle body (22), about the longitudinal axis of the straight proximal portion of guide catheter (60), thereby further promoting access to various anatomical structures.

By way of further example only, guide catheter (60) may be configured and operable in accordance with at least some of the teachings of U.S. patent application Ser. No. 15/852,470, entitled "Dilation Instrument with Guide Catheter Type Sensor," filed Dec. 22, 2017, now abandoned, the disclosure of which is incorporated by reference herein; U.S. Pub. No. 2017/0120020, entitled "Apparatus for Bending Malleable Guide of Surgical Instrument," published May 4, 2017, issued as U.S. Pat. No. 10,137,286 on Nov. 27, 2018, the disclosure of which is incorporated by reference herein; and/or U.S. Pat. App. No. 62/555,841, entitled "Adjustable Instrument for Dilation of Anatomical Passageway," filed Sep. 8, 2017, the disclosure of which is incorporated by reference herein.

Figure 1B:
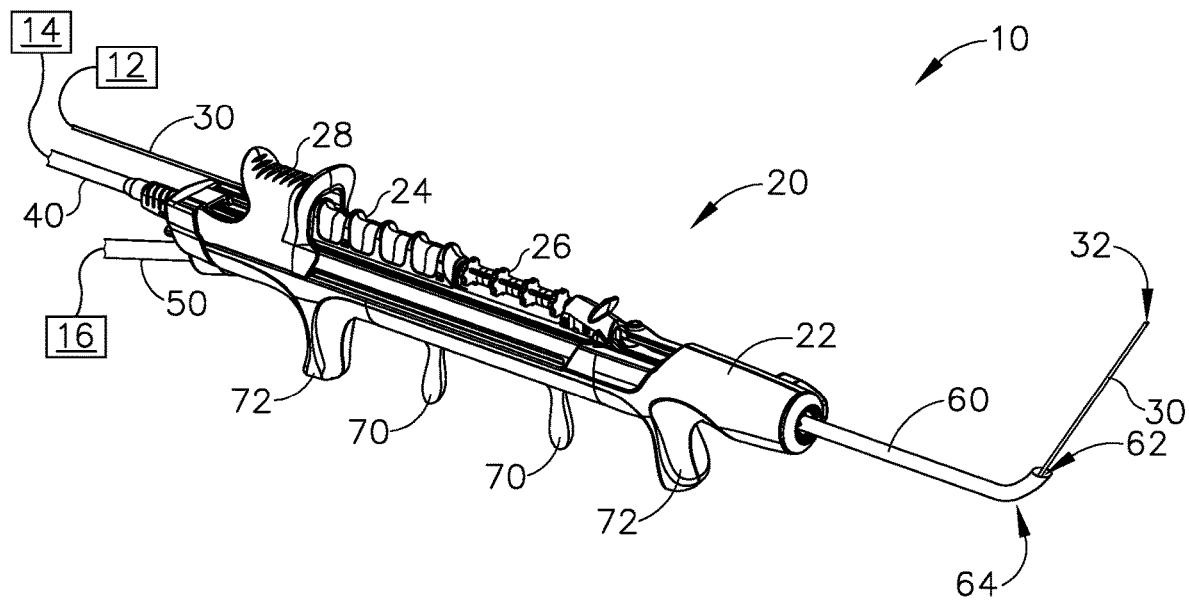
FIG. 1B depicts a perspective view of the dilation instrument system of FIG. 1A, showing the guidewire in a distal position, and the dilation catheter in the proximal position.

A guidewire (30) is coaxially disposed in guide catheter (60). Guidewire slider (24) is secured to guidewire (30). Translation of guidewire slider (24) relative to handle body (22) from a proximal position (FIG. 1A) to a distal position (FIG. 1B) thus causes corresponding translation of guidewire (30) relative to handle body (22) from a proximal position (FIG. 1A) to a distal position (FIG. 1B). When guidewire (30) is in a distal position, a distal portion of guidewire (30) protrudes distally from open distal end (62) of guide catheter (60). Guidewire spinner (26) is operable to rotate guidewire (30) about the longitudinal axis of guidewire (30). Guidewire spinner (26) is coupled with guidewire slider (24) such that guidewire spinner (26) translates longitudinally with guidewire slider (24).

By way of further example only, guidewire (30) may be configured and operable in accordance with at least some of the teachings of U.S. patent application Ser. No. 15/861,959, entitled "Navigation Guidewire with Interlocked Coils," filed Jan. 4, 2018, issued as U.S. Pat. No. 10,610,308 on Apr. 7, 2020, the disclosure of which is incorporated by reference herein; U.S. Pat. No. 9,155,492, entitled "Sinus Illumination Lightwire Device," issued Oct. 13, 2015, the disclosure of which is incorporated by reference herein; U.S. patent application Ser. No. 15/852,530, entitled "Reusable Navigation Guidewire," filed Dec. 22, 2017, published as U.S. Pub. No. 2019/0192177 on Jun. 27, 2019, now abandoned, the disclosure of which is incorporated by reference herein;

U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein; and/or U.S. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

Figure 1C:
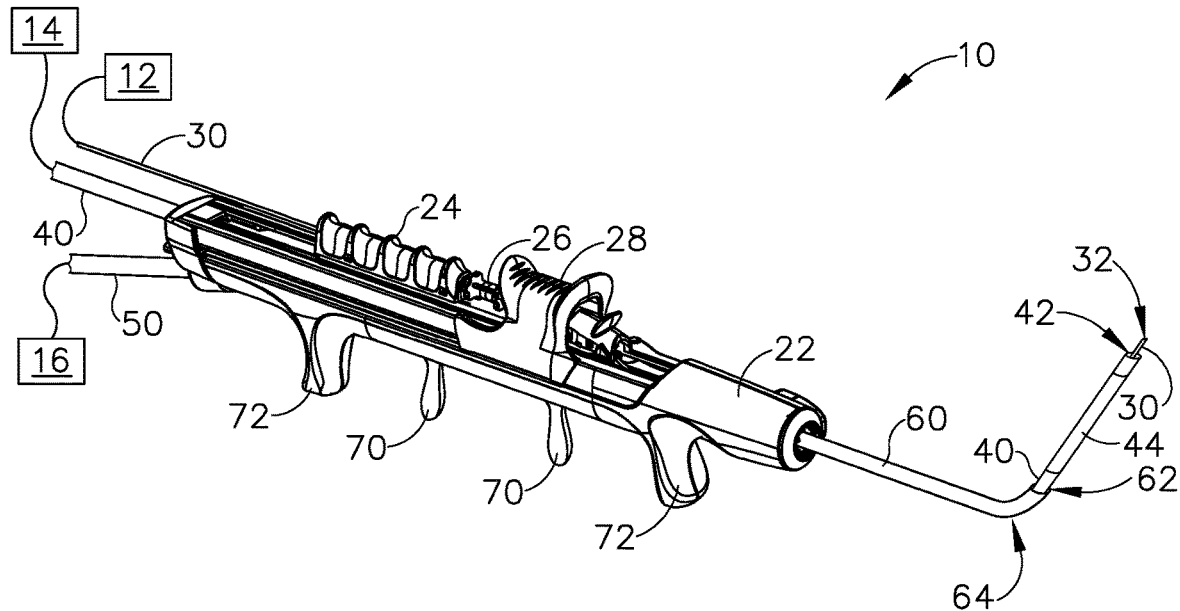
FIG. 1C depicts a perspective view of the dilation instrument system of FIG. 1A, showing the guidewire in the distal position, the dilation catheter in a distal position, and a dilator in a non-dilated state.
Figure 1D:
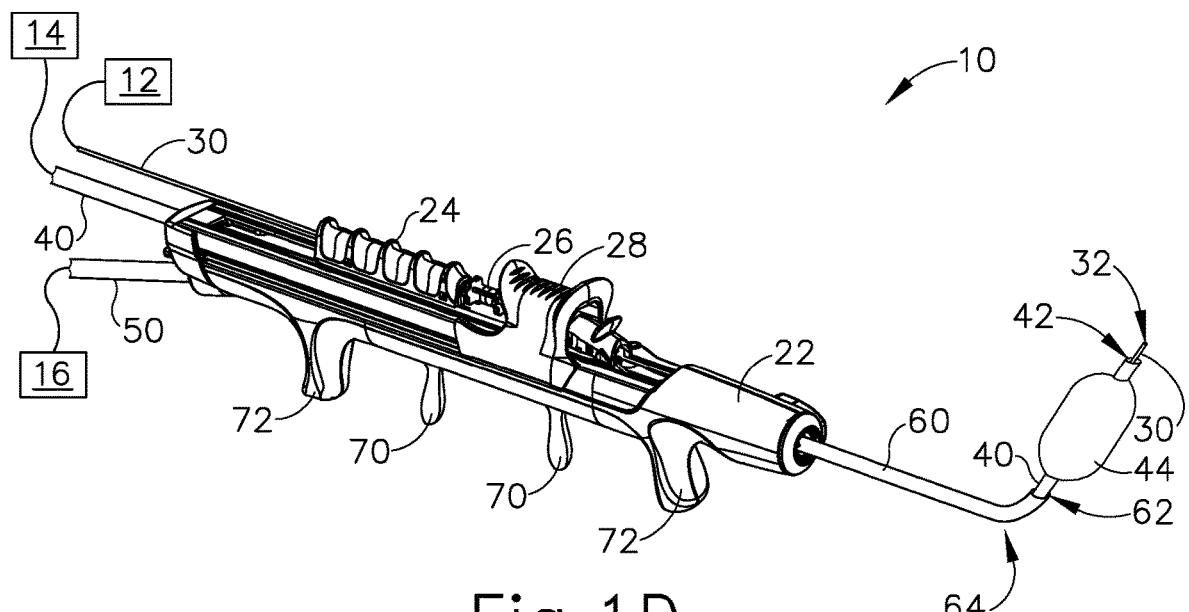
FIG. 1D depicts a perspective view of the dilation instrument system of FIG. 1A, showing the guidewire in the distal position, the dilation catheter in the distal position, and the dilator in a dilated state.

A dilation catheter (40) is coaxially disposed in guide catheter (60). Dilation catheter slider (28) is secured to dilation catheter (40). Translation of dilation catheter slider (28) relative to handle body (22) from a proximal position (FIG. 1B) to a distal position (FIG. 1C) thus causes corresponding translation of dilation catheter (40) relative to handle body (22) from a proximal position (FIG. 1B) to a distal position (FIG. 1C). When dilation catheter (40) is in a distal position, a distal portion of dilation catheter (40) protrudes distally from open distal end (62) of guide catheter (60). Dilation catheter (40) of the present example comprises a non-extensible balloon (44) located just proximal to open distal end (42) of dilation catheter (40). Balloon (44) is in fluid communication with inflation fluid source (14). Inflation fluid source (14) is configured to communicate fluid (e.g., saline, etc.) to and from balloon (44) to thereby transition balloon (44) between a non-inflated state and an inflated state. FIG. 1C shows balloon (44) in a non-inflated state. FIG. 1D shows balloon (44) in an inflated state. In the non-inflated state, balloon (44) is configured to be inserted into a constricted anatomical passageway (e.g., paranasal sinus ostium, Eustachian tube, etc.). In the inflated state, balloon (44) is configured to dilate the anatomical passageway in which balloon (44) is inserted. Other features and operabilities that may be incorporated into dilation catheter (40) will be described in greater detail below.

In some versions, inflation fluid source (14) comprises a manually actuated source of pressurized fluid. In some such versions, the manually actuated source of pressurized fluid may be configured and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein. Other suitable configurations that may be used to provide a source of pressurized fluid will be apparent to those of ordinary skill in the art in view of the teachings herein.

In some instances, it may be desirable to irrigate an anatomical site. For instance, it may be desirable to irrigate a paranasal sinus and nasal cavity after dilation catheter (40) has been used to dilate an ostium or other drainage passageway associated with the paranasal sinus. Such irrigation may be performed to flush out blood, etc. that may be present after a dilation procedure. In some such cases, guide catheter (60) may be allowed to remain in the patient while guidewire (30) and dilation catheter (40) are removed. A dedicated irrigation catheter (not shown) may then be inserted into guide catheter (60) and coupled with irrigation fluid source (16) via irrigation tube (50), to enable irrigation of the anatomical site in the patient. By way of example only, a dedicated irrigation catheter may be configured and operable in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, now abandoned, the disclosure of which is incorporated by reference herein.

II. EXEMPLARY DILATION PROCEDURES

As noted above, dilation instrument system (10) may be used to dilate a drainage passageway associated with a paranasal sinus, a Eustachian tube, and/or any other passageway in the ear, nose, or throat of a patient. The following describes two merely illustrative examples of dilation procedures in which dilation instrument system (10) may be used. The following examples are not intended to be limiting. Other procedures in which dilation instrument system (10) may be used will be apparent to those of ordinary skill in the art in view of the teachings herein.

A. Exemplary Sinus Ostium Dilation Procedure

FIGS. 2A-2B show portions of dilation instrument system (10) being used in an exemplary procedure do dilate an ostium (O) of a maxillary sinus (MS) of a patient. As shown in FIG. 2A, guide catheter (60) is positioned in the nasal cavity (NC) of the patient and is oriented to direct dilation catheter (40) into the ostium (O) of the maxillary sinus (MS). Guidewire (30) is advanced into the maxillary sinus (MS) at the stage depicted in FIG. 2A, and balloon (44) is inflated at the stage depicted in FIG. 2A.

In the steps leading up to the stage depicted in FIG. 2A, dilation catheter (40) may be fully retracted into guide catheter (60), and guidewire (30) may be retracted into dilation catheter (40), as guide catheter (60) is initially inserted into the nasal cavity (NC). Guide catheter (60) may then be manipulated to orient distal end (62) toward the ostium (O) of the maxillary sinus (MS). This may be performed under visualization from an endoscope or otherwise. Guidewire (30) may then be advanced through the ostium (O) and into the maxillary sinus (MS). In versions where guidewire (30) has an illuminating distal end, the position of guidewire (30) in the maxillary sinus (MS) may be verified by observing transillumination effects through the cheek of the patient over the maxillary sinus (MS). In versions where guidewire (30) includes a navigation sensor, an image guided surgery navigation system (or other kind of navigation system) may be used to verify that guidewire (30) is in the maxillary sinus (MS). Once guidewire (30) has been positioned, dilation catheter (40) may be advanced distally along guidewire (30), with further guidance from guide catheter (60), until balloon (44) is positioned in the ostium (O) of the maxillary sinus (MS). The balloon (44) is then inflated to thereby dilate the ostium (O) of the maxillary sinus (MS).

After balloon (44) has been inflated and deflated a sufficient number of times within the ostium (O), dilation instrument system (10) is removed from the patient. The patient then has a dilated ostium (O) as shown in FIG. 2B. The dilated ostium (O) may provide improved ventilation to the maxillary sinus (MS) from the nasal cavity (NC) and/or improved drainage from the maxillary sinus (MS) into the nasal cavity (NC).

B. Exemplary Eustachian Tube Dilation Procedure

Figure 3A:
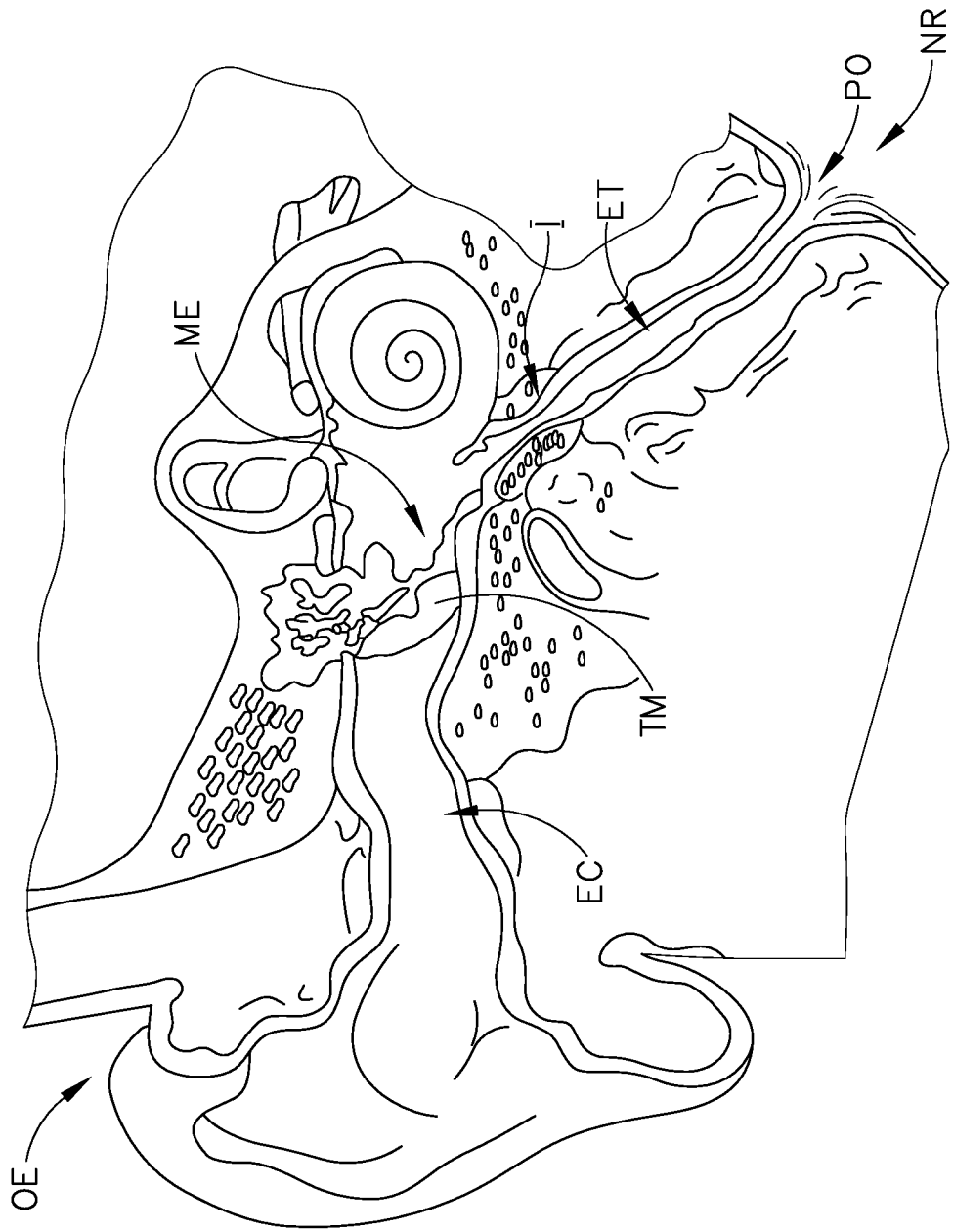
FIG. 3A depicts a cross-sectional view of a human ear showing the inner, middle and outer ear portions and the Eustachian tube connecting the middle ear with the nasopharynx region of the throat.

FIG. 3A shows anatomical structures associated with a patient's ear, including the outer ear (OE), the ear canal (EC), the tympanic membrane (TM), the middle ear (ME), and the Eustachian tube (ET). The Eustachian tube (ET) is in fluid communication with the nasopharynx via the pharyngeal ostium (PO). The isthmus (I) is a narrowed region (e.g., approximately 1 mm in diameter) between the Eustachian tube (ET) and the middle ear (ME). The Eustachian tube (ET) provides a pathway for ventilation from the nasopharynx to the middle ear (ME); and for drainage from the middle ear (ME) to the nasopharynx. When functioning properly, the Eustachian tube (ET) may open for a fraction of a second periodically in response to swallowing or yawning. In so doing, it allows air into the middle ear (ME) to replace air that has been absorbed by the middle ear lining (mucous membrane) or to equalize pressure changes occurring on altitude changes. In instances where fluid is built up in the middle ear (ME), an opened Eustachian tube (ET) also provides a pathway for such fluid to drain from the middle ear (ME) into the nasopharynx.

Figure 3B:
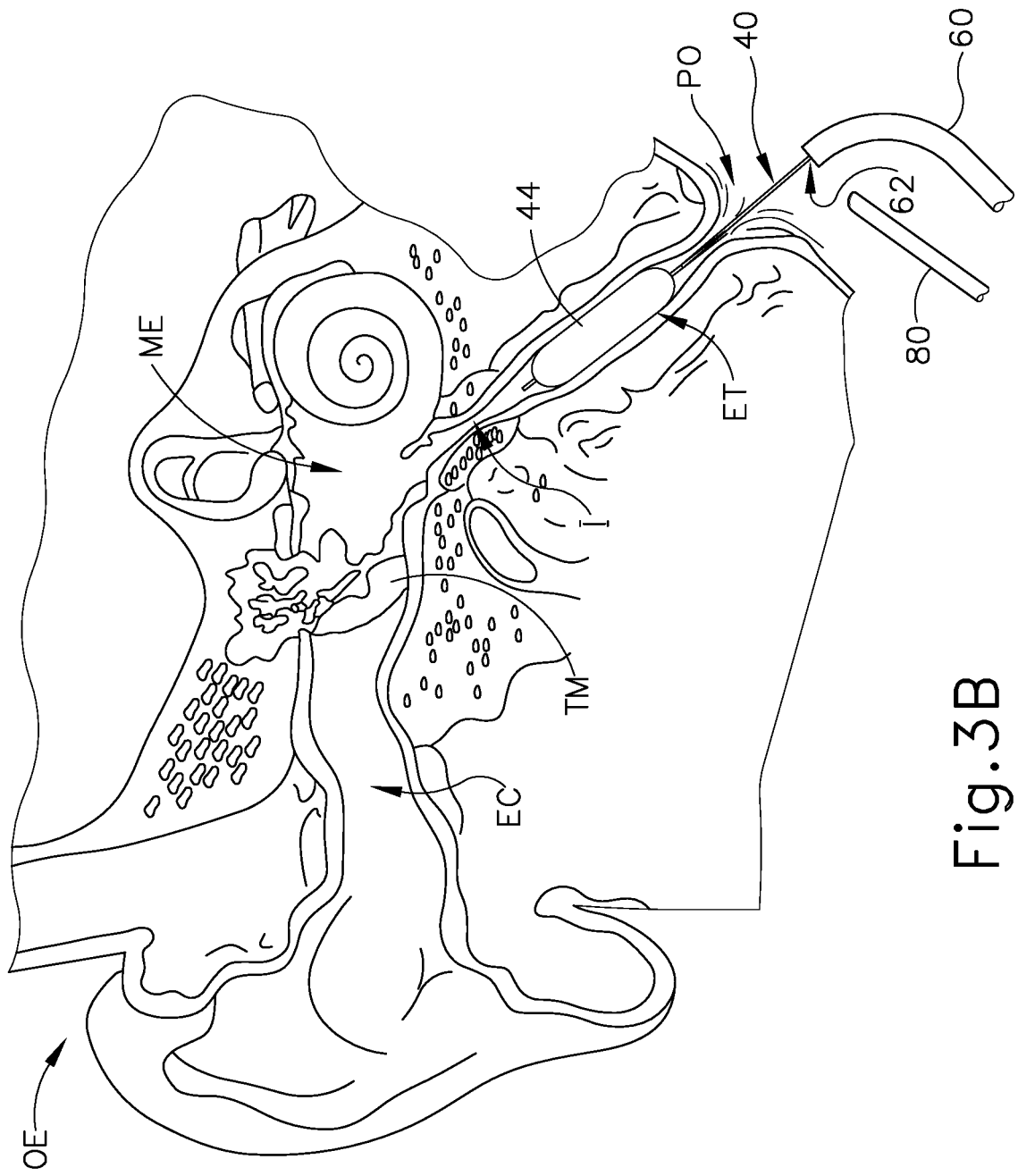
FIG. 3B depicts a cross-sectional view of the human ear of FIG. 3A, with the dilation catheter of the dilation instrument system of FIG. 1A inserted in the Eustachian tube, and the dilator being expanded to dilate the Eustachian tube.

In scenarios where the Eustachian tube (ET) remains persistently blocked or fails to open when it should, it may be desirable to dilate the Eustachian tube (ET). As shown in FIG. 3B, this may be carried out using dilation instrument system (10) by inserting guide catheter (60) through a patient's nose or mouth and positioning guide catheter (60) in the nasopharynx such that distal end (62) is oriented toward the pharyngeal ostium (PO). This may be performed under visualization from an endoscope (80), if desired. Dilation catheter (40) may be advanced through guide catheter (60) to position balloon (44) within the Eustachian tube (ET), and the balloon (44) may then be inflated to thereby dilate the Eustachian tube (ET).

When dilation catheter (40) is advanced through guide catheter (60) to position balloon (44) within the Eustachian tube (ET), it may be necessary to take great care to avoid traversing the isthmus (I). This may ensure that instrumentation does not enter the middle ear (ME) and thereby damage the sensitive anatomical structures within the middle ear (ME). To that end, in the present example, guidewire (30) is not advanced through Eustachian tube (ET) before dilation catheter (40) is advanced into the Eustachian tube (ET). This is because guidewire (30) has a relatively small outer diameter, which may present a substantial risk of guidewire (30) being accidentally advanced through the isthmus (I) and into the middle ear (ME). It may also be desirable to include a structural feature at the distal end of dilation catheter (40) to prevent the distal end of dilation catheter (40) from traversing the isthmus (I). An example of such a structural feature is described in greater detail below.

III. EXEMPLARY ALTERNATIVE DILATION CATHETER

It may be desirable to provide a dilation instrument system (10) with a single dilation catheter that may be used to dilate sinus ostia (O) and other passageways associated with drainage of paranasal sinus cavities and also a Eustachian tube. As noted above, it may be desirable to include a structural feature at the distal end of dilation catheter (40) to prevent the distal end of dilation catheter (40) from traversing the isthmus (I), thereby preventing the distal end of dilation catheter (40) from inadvertently damaging delicate anatomical structures in the middle ear (ME). However, including such a structure on the distal end of dilation catheter (40) prevent the distal end of dilation catheter from traversing a sinus ostium (O) or other passageway associated with drainage of a paranasal sinus. In other words, in order to be large enough to effectively prevent traversal of the isthmus (I), the distal end structure of dilation catheter (40) may be too large to pass through a sinus ostium (O) or other passageway associated with drainage of a paranasal sinus.

In view of the foregoing, it may be desirable to provide a version of dilation catheter (40) that is capable of operating in two different structural modes-one with an enlarged distal end structure and one with a non-enlarged distal end structure. This may facilitate use of the same single dilation catheter in sinus ostium (O) dilation procedures and in Eustachian tube (ET) dilation procedures, while preventing inadvertent traversal of the isthmus (I) during Eustachian tube (ET) dilation procedures, and while enabling traversal of a sinus ostium (O) during sinus ostium (O) dilation procedures. Examples such variations of dilation catheter (40) are described in greater detail below.

Figure 4:
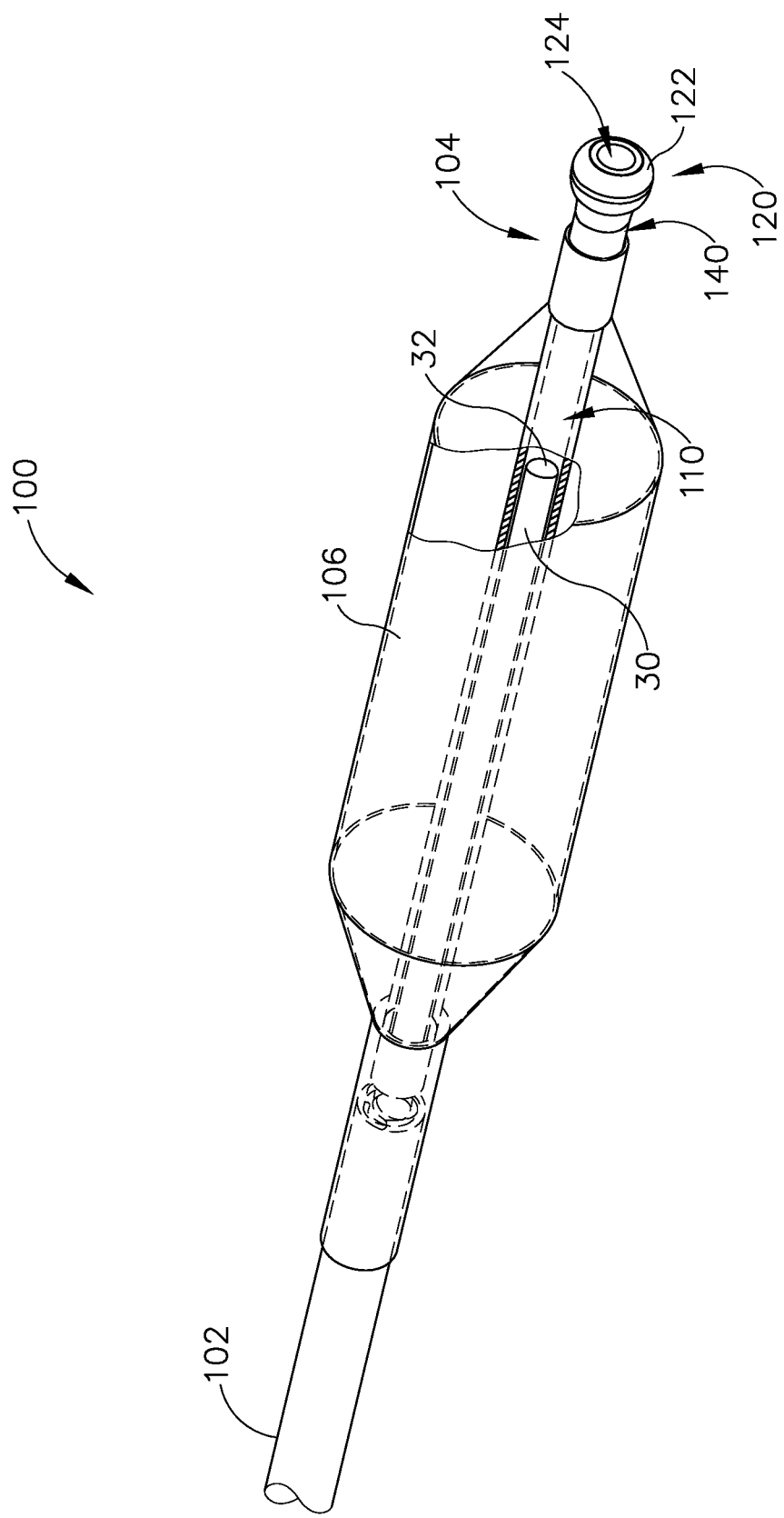
FIG. 4 depicts a perspective view of a distal portion of an exemplary alternative dilation catheter that may be readily incorporated into the dilation instrument system of FIG. 1A, with a bulb tip secured at the distal end of the dilation catheter.

FIGS. 4-5C depict a distal portion of an exemplary alternative dilation catheter (100). Dilation catheter (100) of this example may be readily incorporated into dilation instrument system (10) in place of dilation catheter (40). Dilation catheter (100) of this example comprises a flexible shaft (102) with a distal end (104). An inflatable balloon (106) is secured to shaft (102) near distal end (104). Flexible shaft (102) defines a guidewire lumen (110) that slidably receives guidewire (30). Flexible shaft (102) also defines an inflation lumen (not shown) that provides a pathway for communication of fluid between inflation fluid source (14) and balloon (106).

As shown in FIG. 4, distal end (104) includes a bulbous tip (120), which is secured to the distal end of flexible shaft (102). Bulbous tip (120) includes a bulbous body (122) defining an opening (124). Bulbous body (122) is sized such that bulbous body (122) is too large to pass through an isthmus (I) between a Eustachian tube (ET) and a middle ear (ME). By way of example only, bulbous body (122) may have an outer diameter that is larger than 1 mm, such as 2 mm, 3 mm, or larger. In any case, bulbous body (122) has an outer diameter that is larger than the outer diameter of the distal portion of flexible shaft (102) to which bulbous body (122) is secured. In some versions, bulbous body (122) is shaped like a blueberry. In some other versions, bulbous body (122) is spherical. Alternatively, bulbous body (122) may have any other suitable shape.

In the present example, bulbous body (122) is solid and is formed of a material (e.g., plastic, etc.) that has sufficient rigidity to prevent bulbous body (122) from compressing when bulbous body (122) is pushed into an isthmus (I) of a Eustachian tube (ET) via the Eustachian tube (ET). Bulbous body (122) is thus strong enough to provide a hard stop when an operator advances dilation catheter (100) into a Eustachian tube (ET) to the point where bulbous body (122) engages the isthmus (I). However, bulbous body (122) may still be soft enough to prevent damage to the isthmus (I) when bulbous body (122) engages the isthmus (I) when dilation catheter is inserted into the Eustachian tube (ET).

Opening (124) is in fluid communication with lumen (110) of shaft (102). Opening (124) and lumen (110) thus provide a ventilation pathway for the region of the Eustachian tube (ET) that is distal to balloon (106) when balloon (106) is inflated to dilate the Eustachian tube (ET). In some versions, the diameter of opening (124) is smaller than the outer diameter of guidewire (30), such that bulbous tip (120) prevents distal end (32) of guidewire (30) from exiting distal end (104) of dilation catheter (100) when bulbous tip (120) is secured at distal end (104) of dilation catheter (100). By way of example only, in some versions opening (124) has a diameter of approximately 0.8 mm, with guidewire (30) having an outer diameter of approximately 0.94 mm, and with lumen (110) having a diameter of at least approximately 1 mm.

Dilation catheter (100) also includes a mark (140) that provides a visual indication between the distal end of balloon (106) and the proximal end of bulbous tip (120). In some versions, mark (140) simply provides visual guidance to an operator where to cut dilation catheter (100) when the operator wishes to remove bulbous tip (120) as described in greater detail below. In some other versions, dilation catheter (100) may also include perforations or other weakening structural features that facilitate frangibly breaking bulbous tip (120) away from dilation catheter (100).

FIGS. 4 and 5A show dilation catheter (100) in a mode where dilation catheter (100) is particularly suited for use in procedures to dilate the Eustachian tube (ET). In this mode, bulbous tip (120) is secured to the distal end of shaft (102). When the operator advances dilation catheter (100) into the Eustachian tube (ET) to thereby position balloon (106) into the Eustachian tube (ET), similar to what is shown in FIG. 3B, bulbous body (122) may eventually engage the isthmus (I) thereby arresting further advancement of dilation catheter (100) into the Eustachian tube (ET). This arresting of further advancement may further provide tactile feedback to the operator, indicating that balloon (106) is positioned in the Eustachian tube (ET). The operator may then inflate balloon (106) to thereby dilate the Eustachian tube (ET). During this time, to the extent that guidewire (30) is even positioned within lumen (110) of shaft (102), guidewire (30) may be positioned such that distal end (32) of guidewire (30) is proximal to bulbous tip (120).

After the operator has finished dilating the Eustachian tube (ET), the operator may then wish to dilate a sinus ostium (O) or other passageway associated with drainage of a paranasal sinus. To facilitate such an operation, the operator may remove bulbous tip (120) at mark (140). In some instances, this removal may comprise cutting dilation catheter (100) at mark (140). In some other instances, this removal may comprise breaking dilation catheter (100) at mark (140). In any case, after bulbous tip (120) is removed, dilation catheter (100) may appear as shown in FIG. 5B. At this point, dilation catheter (100) as an open distal end (150) that is proximal to the location where bulbous tip (120) was located. This open distal end (150) provides sufficient clearance for distal end (32) of guidewire (30) to pass freely through open distal end (150) of dilation catheter, as shown in FIG. 5C. With dilation catheter (100) in the mode shown in FIGS. 5B-5C, distal end (150) may also pass through a sinus ostium (O) or other passageway associated with drainage of a paranasal sinus, thereby facilitating use of dilation catheter (100) to perform the procedure shown in FIG. 2A.

Figure 6A:
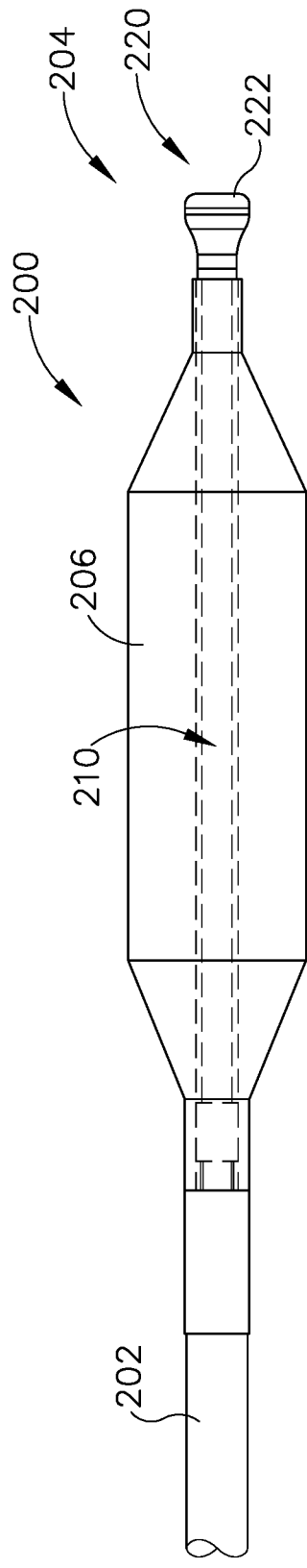
FIG. 6A depicts a side elevational view of the distal portion of another exemplary alternative dilation catheter that may be readily incorporated into the dilation instrument system of FIG. 1A, with a bulb tip secured at the distal end of the dilation catheter.
Figure 6B:
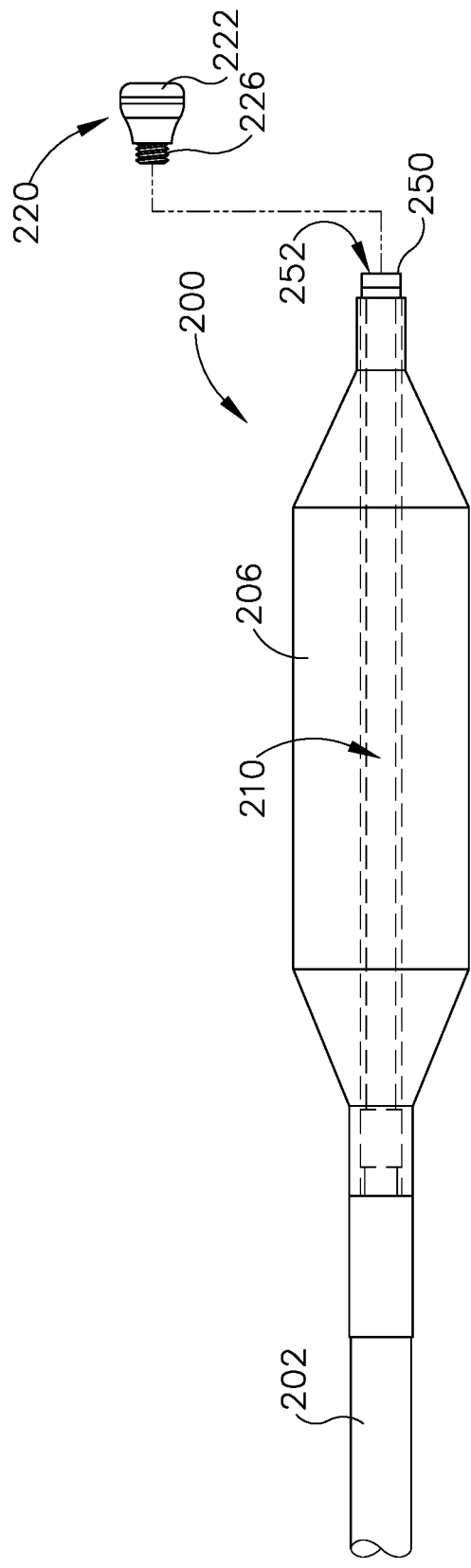
FIG. 6B depicts a side elevational view of the distal portion of the dilation catheter of FIG. 6A, with the bulb tip removed from the distal end of the dilation catheter.

In the foregoing example, if an operator wishes to use dilation catheter (100) in both a Eustachian tube (ET) dilation procedure and a sinus ostium (O) dilation procedure, the operator must perform the Eustachian tube (ET) dilation procedure first. After the operator removes bulbous tip (120) to perform a sinus ostium (O) dilation procedure, it may not be possible to re-attach bulbous tip (120) to facilitate performance of a subsequent Eustachian tube (ET) dilation procedure. It may therefore be desirable to provide a variation of dilation catheter (100) in which a removed bulbous tip (120) may be re-attached to dilation catheter (100). An example of such a variation is shown in FIGS. 6A-6B, which depict a distal portion of another exemplary alternative dilation catheter (200). Dilation catheter (200) of this example may be readily incorporated into dilation instrument system (10) in place of dilation catheter (40). Dilation catheter (200) of this example comprises a flexible shaft (202) with a distal end (204). An inflatable balloon (206) is secured to shaft (202) near distal end (204). Flexible shaft (202) defines a guidewire lumen (210) that slidably receives guidewire (30) (though guidewire (30) is not shown in FIGS. 6A-6B). Flexible shaft (202) also defines an inflation lumen (not shown) that provides a pathway for communication of fluid between inflation fluid source (14) and balloon (206).

Distal end (204) includes a bulbous tip (220), which is secured to the distal end of flexible shaft (202). Bulbous tip (220) includes a bulbous body (222) defining an opening. While the opening of bulbous body (222) is not shown in FIGS. 6A-6B, the opening of bulbous body (222) may be sized and configure just like opening (124) described above. Bulbous body (222) is sized such that bulbous body (222) is too large to pass through an isthmus (I) between a Eustachian tube (ET) and a middle ear (ME). By way of example only, bulbous body (222) may have an outer diameter that is larger than 1 mm, such as 2 mm, 3 mm, or larger. In any case, bulbous body (222) has an outer diameter that is larger than the outer diameter of the distal portion of flexible shaft (202) to which bulbous body (222) is secured. In some versions, bulbous body (222) is shaped like a blueberry. In some other versions, bulbous body (222) is spherical. Alternatively, bulbous body (222) may have any other suitable shape.

In the present example, bulbous body (222) is solid and is formed of a material (e.g., plastic, etc.) that has sufficient rigidity to prevent bulbous body (222) from compressing when bulbous body (122) is pushed into an isthmus (I) of a Eustachian tube (ET) via the Eustachian tube (ET). Bulbous body (222) is thus strong enough to provide a hard stop when an operator advances dilation catheter (200) into a Eustachian tube (ET) to the point where bulbous body (222) engages the isthmus (I).

In the present example, bulbous tip (220) is secured to shaft (202) via a threaded coupling, which enables bulbous tip (220) to be selectively detached from and re-attached to shaft (202). As shown in FIG. 6B, a male threaded feature (226) is located at the proximal end of bulbous tip (220). A complementary threaded recess (252) is positioned at the distal end (250) of shaft (202). Thus, to transition from a Eustachian tube (ET) dilation mode to a sinus ostium (O) dilation mode, an operator may simply unscrew bulbous tip (220) from shaft (202). Conversely, to transition from a sinus ostium (O) dilation mode to a Eustachian tube (ET) dilation mode, an operator may screw bulbous tip (220) onto shaft (202). While a threaded coupling is used in the present example, any other suitable kind of coupling may be used, including but not limited to bayonet mounting features, friction/interference fit features, latching features, snap-fitting features, and/or any other suitable kinds of reversibly coupling features as will be apparent to those of ordinary skill in the art in view of the teachings herein.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a shaft having a proximal end and a distal end, wherein the shaft has a first outer cross-sectional dimension; (b) an expandable dilation member positioned proximal to the distal end of the shaft, wherein the dilation member is operable to transition between a non-expanded configuration and an expanded configuration, wherein the dilation member is sized to pass through a passageway associated with drainage of a paranasal sinus or a Eustachian tube when the dilation member is in the non-expanded configuration; and (c) a bulbous tip positioned at the distal end of the shaft, wherein the bulbous tip is distal to the dilation member, wherein the bulbous tip has a second outer cross-sectional dimension, wherein the second outer cross-sectional dimension is larger than the first outer cross-sectional dimension, wherein the bulbous tip is removably secured to the distal end of the shaft.

Example 2

The apparatus of Example 1, wherein the shaft defines a first lumen, wherein the first lumen is configured to slidably receive a guidewire, wherein the first lumen has a first diameter.

Example 3

The apparatus of Example 2, wherein the bulbous tip defines an opening, wherein the opening is in communication with the first lumen of the shaft.

Example 4

The apparatus of Example 3, wherein the opening has a second diameter, wherein the second diameter is smaller than the first diameter.

Example 5

The apparatus of Example 4, further comprising a guidewire slidably disposed in the first lumen, wherein the guidewire has a third diameter, wherein the first diameter is larger than the third diameter, wherein the third diameter is larger than the second diameter.

Example 6

The apparatus of any one or more of Examples 2 through 5, wherein the dilation member further comprises a balloon.

Example 7

The apparatus of Example 6, wherein the shaft defines a second lumen, wherein the second lumen is configured to communicate an inflation fluid to the balloon.

Example 8

The apparatus of any one or more of Examples 1 through 7, further comprising a marking on the shaft, wherein the marking is positioned and configured to indicate a longitudinal position located between a distal end of the dilation member and a proximal end of the bulbous tip.

Example 9

The apparatus of any one or more of Examples 1 through 8, wherein the shaft further comprises a weakened portion configured to facilitate breaking of the bulbous tip away from the distal end of the shaft.

Example 10

The apparatus of any one or more of Examples 1 through 8, further comprising a threaded coupling, wherein the threaded coupling removably joins the bulbous tip to the distal end of the shaft.

Example 11

The apparatus of any one or more of Examples 1 through 10, wherein the bulbous tip comprises a body having a blueberry shape.

Example 12

The apparatus of any one or more of Examples 1 through 11, wherein the bulbous tip is formed of a plastic material.

Example 13

The apparatus of any one or more of Examples 1 through 12, further comprising a guide catheter, wherein the shaft is slidably disposed in the guide catheter.

Example 14

The apparatus of Example 13, wherein the guide catheter defines a bend, wherein the bend is configured to guide the distal end of the shaft into a passageway associated with drainage of a paranasal sinus or a Eustachian tube.

Example 15

The apparatus of any one or more of Examples 1 through 14, wherein the dilation member is configured to dilate a passageway associated with drainage of a paranasal sinus or a Eustachian tube when the dilation member is in the expanded configuration.

Example 16

A method comprising: (a) advancing a dilation catheter into a Eustachian tube of a patient via a pharyngeal ostium of the patient; (b) engaging an isthmus of the Eustachian tube with a bulbous tip at the distal end of the dilation catheter; (c) ceasing advancement of the dilation catheter in the Eustachian tube in response to the engagement of the isthmus with the bulbous tip; (d) expanding a dilator of the dilation catheter in the Eustachian tube to thereby dilate the Eustachian tube; (e) removing the dilation catheter from the Eustachian tube; (f) removing the bulbous tip from the dilation catheter; (g) advancing the dilation catheter into a nasal cavity of the patient; (h) positioning the dilator in a passageway associated with drainage of a paranasal sinus of the patient; and (i) expanding the dilator to thereby dilate the passageway associated with drainage of the paranasal sinus.

Example 17

The method of Example 16, further comprising advancing a guidewire through the dilation catheter and out through an open distal end of the dilation catheter to thereby position the guidewire in the passageway associated with drainage of the paranasal sinus, wherein the act of positioning the dilator in a passageway associated with drainage of the paranasal sinus of the patient comprises advancing the dilator along the guidewire.

Example 18

The method of any one or more of Examples 16 through 17, further comprising re-attaching the bulbous tip to the dilation catheter after performing the act of expanding the dilator to thereby dilate the passageway associated with drainage of the paranasal sinus.

Example 19

A method comprising: (a) advancing a dilator of a dilation catheter through a nasal cavity of a patient and into a passageway associated with drainage of a paranasal sinus of the patient; (b) expanding the dilator to thereby dilate the passageway associated with drainage of the paranasal sinus; (c) removing the dilation catheter from the nasal cavity; (d) securing a bulbous tip to a distal end of the dilation catheter; (e) advancing the dilation catheter into a Eustachian tube of the patient via a pharyngeal ostium of the patient; (f) engaging an isthmus of the Eustachian tube with the bulbous tip at the distal end of the dilation catheter; (g) ceasing advancement of the dilation catheter in the Eustachian tube in response to the engagement of the isthmus with the bulbous tip; and (h) expanding the dilator in the Eustachian tube to thereby dilate the Eustachian tube.

Example 20

The method of Example 19, wherein the act of securing the bulbous tip to the distal end of the dilation catheter comprises screwing the bulbous tip and the distal end of the dilation catheter together via a threaded coupling.

V. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A method comprising:
   (a) advancing a dilation catheter into a Eustachian tube of a patient via a pharyngeal ostium of the patient;
   (b) engaging an isthmus of the Eustachian tube with a bulbous tip at a distal end of the dilation catheter;
   (c) ceasing advancement of the dilation catheter in the Eustachian tube in response to the engagement of the isthmus with the bulbous tip;
   (d) expanding a dilator of the dilation catheter in the Eustachian tube to thereby dilate the Eustachian tube;
   (e) removing the dilation catheter from the Eustachian tube;
   (f) removing the bulbous tip from the dilation catheter;
   (g) advancing the dilation catheter into a nasal cavity of the patient;

(h) positioning the dilator in a passageway associated with drainage of a paranasal sinus of the patient; and (i) expanding the dilator to thereby dilate the passageway associated with drainage of the paranasal sinus.

2. The method of claim 1, further comprising advancing a guidewire through the dilation catheter and out through an open distal end of the dilation catheter to thereby position the guidewire in the passageway associated with drainage of the paranasal sinus, wherein the act of positioning the dilator in a passageway associated with drainage of the paranasal sinus of the patient comprises advancing the dilator along the guidewire.

3. The method of claim 2, further comprising locating a navigation sensor on the guidewire by using a surgery navigation system while positioning the guidewire in the passageway associated with drainage of the paranasal sinus.

4. The method of claim 2, wherein advancing a guidewire through the dilation catheter and out through an open distal end of the dilation catheter further includes providing a user with a location of the guidewire relative to the paranasal sinus of the patient.

5. The method of claim 4, wherein providing a user with the location of the guidewire relative to the paranasal sinus of the patient is performed by illuminating a distal end of the guidewire.

6. The method of claim 1, further comprising re-attaching the bulbous tip to the dilation catheter after performing the act of expanding the dilator to thereby dilate the passageway associated with drainage of the paranasal sinus.

7. The method of claim 1, further comprising visualizing the dilation catheter using an endoscope.

8. The method of claim 1, wherein expanding the dilator is performed by injecting pressurized saline into the dilator from an inflation fluid source.

9. The method of claim 1, wherein advancing the dilation catheter, removing the dilation catheter, and positioning the dilator are performed by a user using one hand.

10. The method of claim 1, further comprising irrigating an anatomical site via the dilation catheter.

11. The method of claim 1, further comprising restricting a guidewire from advancing past the bulbous tip while the bulbous tip is attached to the dilation catheter.

12. The method of claim 1, wherein the bulbous tip ventilates the Eustachian tube during dilation of the Eustachian tube and prevents a guidewire from advancing beyond the bulbous tip.

13. The method of claim 1, wherein removing the bulbous tip from the dilation catheter is performed at a marked position configured to indicate a longitudinal position located between a distal end of the dilator and a proximal end of the bulbous tip.

14. The method of claim 1, wherein removing the bulbous tip from the dilation catheter comprises cutting the bulbous tip from the dilation catheter.

15. The method of claim 1, wherein removing the bulbous tip from the dilation catheter comprises breaking the bulbous tip off of the dilation catheter.

16. A method comprising:

(a) advancing a dilator of a dilation catheter through a nasal cavity of a patient and into a passageway associated with drainage of a paranasal sinus of the patient;

(b) expanding the dilator to thereby dilate the passageway associated with drainage of the paranasal sinus;

(c) removing the dilation catheter from the nasal cavity;

(d) securing a bulbous tip to a distal end of the dilation catheter;

(e) advancing the dilation catheter into a Eustachian tube of the patient via a pharyngeal ostium of the patient;

(f) engaging an isthmus of the Eustachian tube with the bulbous tip at the distal end of the dilation catheter;

(g) ceasing advancement of the dilation catheter in the Eustachian tube in response to the engagement of the isthmus with the bulbous tip; and (h) expanding the dilator in the Eustachian tube to thereby dilate the Eustachian tube.

17. The method of claim 16, wherein the act of securing the bulbous tip to the distal end of the dilation catheter comprises screwing the bulbous tip and the distal end of the dilation catheter together via a threaded coupling.

18. The method of claim 16, further comprising deflating the dilator before removing the dilation catheter from the nasal cavity.

19. The method of claim 18, further comprising ventilating the Eustachian tube during dilation of the Eustachian tube with the bulbous tip attached to the distal end of the dilation catheter.

20. A method comprising:

(a) engaging an isthmus of a Eustachian tube with a bulbous tip at a distal end of a dilation catheter;

(b) expanding a dilator of the dilation catheter in the Eustachian tube to thereby dilate the Eustachian tube;

(c) removing the bulbous tip from the dilation catheter;

(d) relocating the dilator to a nasal cavity passageway associated with drainage of a paranasal sinus of a patient;

(e) expanding the dilator to thereby dilate the nasal cavity passageway associated with drainage of the paranasal sinus; and (f) irrigating the nasal cavity passageway via the dilation catheter.

* * * * *